US010657726B1

(12) United States Patent
Jin et al.

(10) Patent No.: US 10,657,726 B1
(45) Date of Patent: May 19, 2020

(54) MIXED REALITY SYSTEM AND METHOD FOR DETERMINING SPATIAL COORDINATES OF DENTAL INSTRUMENTS

(71) Applicants: Xin Jin, Beijing (CN); Xiaoyu Lu, Covina, CA (US)

(72) Inventors: Xin Jin, Beijing (CN); Xiaoyu Lu, Covina, CA (US)

(73) Assignee: International Osseointegration AI Research and Training Center, Rosemead, CA (US)

( * ) Notice: Subject to any disclaimer, the term of this patent is extended or adjusted under 35 U.S.C. 154(b) by 0 days.

(21) Appl. No.: 16/137,416

(22) Filed: Sep. 20, 2018

Related U.S. Application Data

(60) Provisional application No. 62/566,841, filed on Oct. 2, 2017.

(51) Int. Cl.
*G06T 19/00* (2011.01)
*G16H 40/63* (2018.01)
*A61B 34/20* (2016.01)
*A61B 34/10* (2016.01)
*G06F 3/01* (2006.01)
*G16H 40/20* (2018.01)

(52) U.S. Cl.
CPC .......... *G06T 19/006* (2013.01); *A61B 34/10* (2016.02); *A61B 34/20* (2016.02); *G06F 3/011* (2013.01); *G16H 40/63* (2018.01); *A61B 2034/2065* (2016.02); *G16H 40/20* (2018.01)

(58) Field of Classification Search
CPC ....... G06T 19/006; G06F 3/011; G16H 40/63; G16H 40/20; A61B 34/20; A61B 34/10; A61B 2034/2065; A61B 2034/2051; A61B 2090/3983
See application file for complete search history.

(56) References Cited

U.S. PATENT DOCUMENTS

| 5,857,853 | A | 2/1999 | van Niferick et al. |
| 6,402,707 | B1 | 6/2002 | Ernest |
| 8,487,962 | B2 | 7/2013 | Quadling et al. |
| 9,844,324 | B2 * | 12/2017 | Merritt ................. A61B 5/0088 |
| 10,105,149 | B2 * | 10/2018 | Haider .................... A61B 17/17 |
| 2005/0020910 | A1 | 1/2005 | Quadling et al. |
| 2005/0182316 | A1 * | 8/2005 | Burdette .............. A61B 8/0833 600/424 |
| 2009/0088634 | A1 * | 4/2009 | Zhao ...................... B25J 9/1689 600/427 |
| 2015/0248793 | A1 | 9/2015 | Abovitz et al. |

(Continued)

FOREIGN PATENT DOCUMENTS

WO WO2017144934 8/2017

*Primary Examiner* — Maurice L. McDowell, Jr.
*Assistant Examiner* — Donna J. Ricks
(74) *Attorney, Agent, or Firm* — Lewis Brisbois Bisgaard & Smith, LLP

(57) ABSTRACT

A mixed reality system and method for determining spatial positions of dental instruments without having a fixed intra oral reference point is disclosed. An intra-oral image sensor-based positioning device including at least two cameras is provided to sense and track the movements of dental instruments being used. The three-dimensional coordinates relating to the movement and orientation of the dental instruments are obtained for real time or delayed use in a mixed reality environment.

3 Claims, 5 Drawing Sheets

(56) References Cited

U.S. PATENT DOCUMENTS

2016/0262716 A1    9/2016  Kravis et al.
2016/0324593 A1*  11/2016  El-Haddad ................ G06T 7/73
2017/0065379 A1    3/2017  Cowburn et al.

* cited by examiner

MIXED REALITY SYSTEM AND METHOD FOR DETERMINING SPATIAL COORDINATES OF DENTAL INSTRUMENTS

RELATED APPLICATION

This application claims the benefit of priority under 35 U.S.C. § 119(e) to Provisional Application No. 62/566,841, filed on Oct. 2, 2017, which is incorporated by reference in its entirety.

STATEMENT REGARDING FEDERALLY SPONSORED RESEARCH OR DEVELOPMENT

Not applicable

INCORPORATION BY REFERENCE OF MATERIAL SUBMIT TED ON A COMPACT DISC

Not applicable

THE NAMES OF THE PARTIES TO A JOINT RESEARCH AGREEMENT

Not applicable

BACKGROUND OF THE INVENTION

This invention relates to a mixed reality system and method for determining spatial coordinates of dental instruments. Mixed reality ("MR") refers to the merging of real and virtual environment to create a new environment and visualization where physical and digital objects co-exist and interact in real time. In the medical space, MR has been used to assist surgeons in planning and performing surgical procedures. Precision and accuracy in a medically related MR environment are of paramount importance because insufficient precision and accuracy could result in serious patient injury.

In the field of dentistry, cameras have been used to provide images of a patient's intra-oral anatomy (such as cranium, maxilla, mandible, and dentition), which are then used to either manufacture dental implants or prostheses or provide stationary positions/locations of intra-oral objects, such as intra-oral mapping. Moreover, in order to provide positioning or mapping data, a reference point is fixed in the patient intra-orally. In performing a dental procedure in an MR environment, however, being able to track positions of an actively moving dental instrument with precision is of paramount importance. Therefore, there is a need to have a system and method for determining the spatial coordinates of dental instruments.

The present invention enables a dental professional to determine the spatial positions of dental instruments (which may be stationary or actively moving) in an MR environment without having a fixed intra oral reference point so that the dental professional may plan, design, and perform an dental procedure to be performed on a patient with precision and accuracy. The present invention includes an intra-oral image sensor-based position detection device. The intra-oral image sensor-based position detection device includes two or more cameras that detect the spatial coordinates of dental instruments, generates data thereof, and provides said data to be used in the MR environment in delayed time or real time. Images of the patient's craniofacial anatomy and the positions of dental instruments are reconstructed and displayed for the dental professional's viewing. Through the various displays the dental professional would be able to accurately control and track the movement of dental instruments to ensure the surgical procedure is performed with precision.

BRIEF SUMMARY OF THE INVENTION

The present invention discloses an intra-oral sensor-based positioning and navigation device positioned in the patient's mouth which senses and tracks the movement and position of dental instruments (which may optionally includes sensors). One of the uses of the present invention is to enable a person to determine the spatial positions of dental instruments (which may be stationary or actively moving) in an MR environment without having a fixed intra oral reference point. The MR environment may be based on a defined space, such as a patient's intra-oral space. The defined space may be defined by a certain number of parallel planes where each plane comprises a certain number of points where each point has a set of three-dimensional coordinates (X, Y, Z). In terms of digital graphic representation, each point may be synonymous to a pixel. If, for example, a 33 mm (millimeter) by 33 mm plane comprises 1280 by 1280 pixels, then each pixel would represent a sub-space of approximately 0.02578 mm (33 mm divided by 1280) by 0.02578 mm within the defined space. Thus, the coordinates of each pixel would represent a certain sub-space within the defined space. If a point of an object, such as a dental instrument, is positioned within a certain sub-space, the coordinates of the pixel for this sub-space can be used to identify the spatial position of the point of the object. If a plane comprises more pixels, each pixel would represent a smaller (or more refined) space, or higher resolution as termed in graphic representation, which would translate to high precision or accuracy.

The three-dimensional coordinates of a position in space may be determined through the use of two or more cameras viewing from different angles. In the case of a two-camera system (Camera 1 and Camera 2), Camera 1 may provide a first set of two-dimensional coordinates relative to Camera 1 for the position on a plane at a certain distance from Camera 1. Then Camera 2 located away from Camera 1 may provide a second set of two-dimensional coordinates relative to Camera 2 for the same position on a plane at a certain distance from Camera 2. Through an algorithm, the three-dimensional coordinate of the position relative to Cameras 1 and 2 may be determined through calculation based on the first and second sets of two-dimensional coordinates.

In one embodiment, the relative position between Cameras 1 and 2 should be fixed. The three-dimensional coordinates of a position (X, Y, Z) is calculated based on the following algorithm/formula sets:

Camera 1:

$$X = A_1 * X_1 - B_1 * Y_1 + X_{01}$$

$$Y = B_1 * X_1 + A_1 * Y_1 + Y_{01}$$

$(X_1, Y_1)$ is the two-dimensional coordinates relative to Camera 1.

Camera 2:

$$X = A_2 * X_2 - B_2 * Y_2 + X_{02}$$

$$Z = B_2 * X_2 + A_2 * Y_2 + Y_{02}$$

$(X_2, Y_2)$ is the two-dimensional coordinates relative to Camera 2.

$A_1, B_1, X_{01}, Y_{01}, A_2, B_2, X_{02}$, and $Y_{02}$ are parameters that need to be determined through calibration. In one embodiment, Cameras 1 and 2 are calibrated by providing four spatial positions with known coordinate numbers X, Y, Z, $X_1, Y_1, X_2$, and $Y_2$. Applying these known numbers to the formula set above, $A_1, B_1, X_{01}, Y_{01}, A_2, B_2, X_{02}$, and $Y_{02}$ can be determined. Once the parameters are determined, the three-dimensional coordinates of any spatial position (X, Y, Z) can be determined based on $(X_1, Y_1)$ and $(X_2, Y_2)$. Accordingly, a database containing the three-dimensional coordinates of every spatial position in a defined space may be established. Once the two cameras sense a point of a dental instrument, i.e., determining $(X_1, Y_1)$ and $(X_2, Y_2)$, through calculating based on the formula set or referencing the established database, the point's three-dimensional coordinates may be obtained in real time and used to display the point's position for viewing. If the point moves, the system and method can calculate and update the point's position in real time. Accordingly, an intra-oral image sensor-based positioning and navigation device having two cameras sensing a dental instrument may determine the spatial position of the dental instrument with precision. Three or more camera could also be used in a similar system with same calibration process described above to determine the three-dimensional coordinates of a position in a wider measurement range.

These and other aspects of this invention will become apparent to those skilled in the art after reviewing the following description of the invention.

BRIEF DESCRIPTION OF THE DRAWINGS

The above-mentioned features and objects of the present disclosure will become more apparent with reference to the following description taken in conjunction with the accompanying drawings wherein like reference numerals denote like elements and in which:

FIG. 1-2 is a graphic representation of plane 13 as shown in FIG. 1-1;

FIG. 2 is a schematic presentation of a two-camera measurement at a distance;

DETAILED DESCRIPTION OF THE INVENTION

For illustrative purpose, the principles of the present invention are described by referring to an exemplary embodiment thereof. Before any embodiment of the invention is explained in detail, it should be understood that the invention is not limited in its application to the details of construction and the arrangement of components set forth in the following description or illustrated in the following drawings. The invention is capable of other embodiments and of being practiced or of being carried out in various ways. Also, it should be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
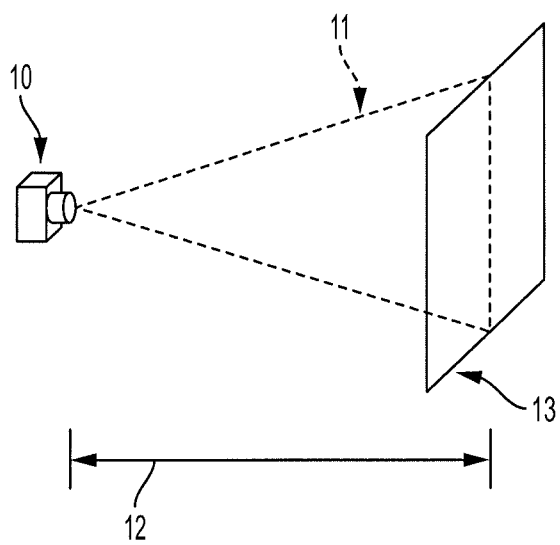
FIG. 1-1 is a schematic presentation of a single camera measurement at a distance.
Figure 2:
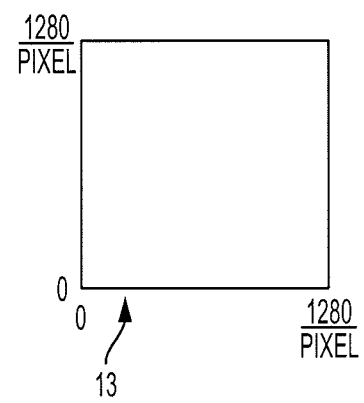
Figure 2:
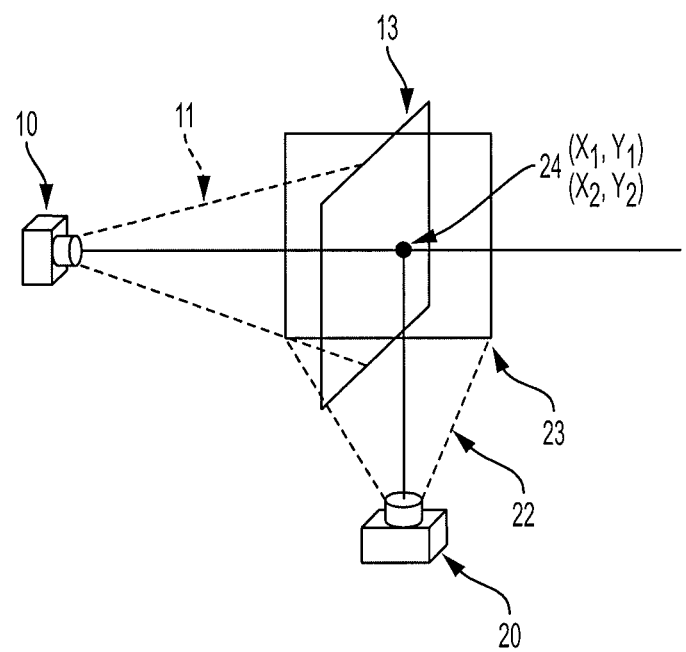

FIG. 1-1 illustrates an embodiment of measurement with a single camera 10 having a field of view 11. Camera 10 may sense a defined plane 13 that is at a known distance 12 from camera 10 and corresponds to (as illustrated here perpendicular to) the field of view 11. The defined plane 13 comprises a matrix of pixels where each pixel has a set of two-dimensional coordinates $(X_1, Y_1)$ relative to the single camera 10. In one embodiment, as illustrated in FIG. 1-2, the defined plane 13 comprises of a matrix of 1280×1280 pixels which corresponds to the 1280×1280 image sensor in Camera 10. If the defined plane 13 is 33 mm by 33 mm in size, each pixel in defined plane 13 would represent a sub-space of approximately 0.02578 mm (33 mm divided by 1280) by 0.02578 mm within the defined plane 13. By changing the distance 12, more defined planes parallel to each other are determined, which in turn forms a defined 3 dimensional space 33 as illustrated in FIG. 3.

In a two-camera measurement, as shown in FIG. 2, a second camera 20 is placed away from the first camera 10. Similarly, Camera 20 has a field of view 21 and may sense a defined plane 23 that is at a known distance 22 from camera 20 and is perpendicular to the field of view 21. The defined plane 23 comprises a matrix of pixels where a pixel 24 would have a set of two-dimensional coordinates $(X_2, Y_2)$ relative to camera 20. The pixel 24, if is also on the defined plane 13, would also have a set of two-dimensional coordinates $(X_1, Y_1)$ relative to camera 10.

Figure 3:
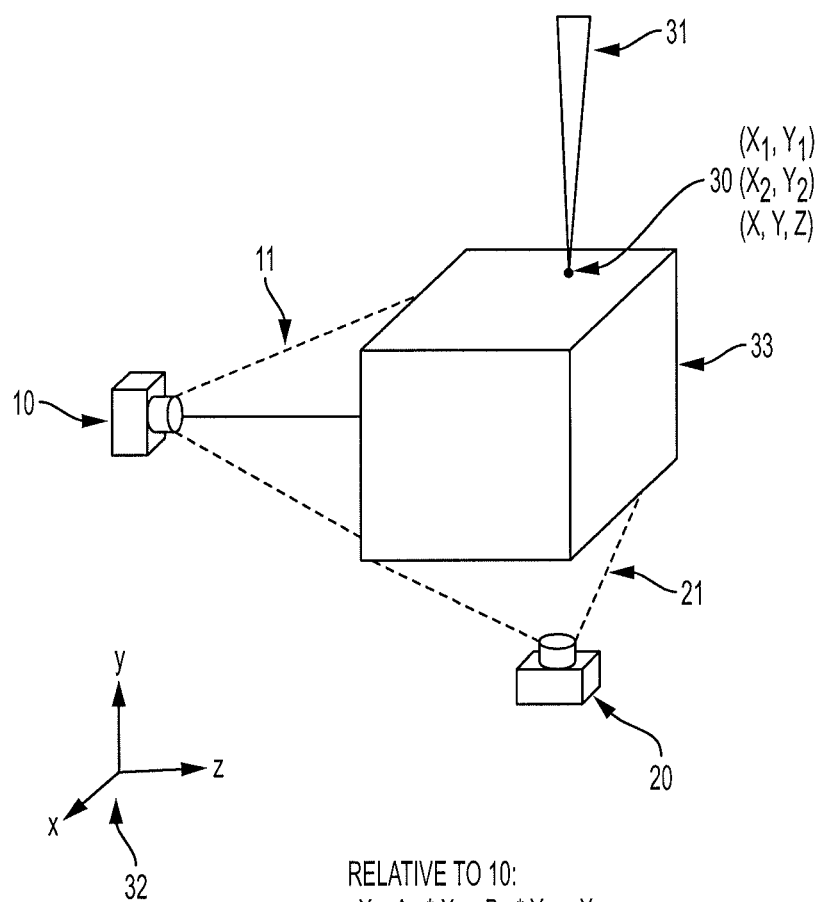
FIG. 3 is a schematic presentation of a two-camera measurement system and an algorithm for determining a spatial position within a defined space.

FIG. 3 shows an embodiment of two-camera measurement system and an algorithm for determining a spatial position within a defined space. The first camera 10 having a field of view 11 and the second camera 20 having a second field of view 21 define a space 33 comprises a matrix of pixels. Based on a selected and known three-dimensional coordinate system 32, a pixel 30 within the space 33 would have a three-dimensional coordinate (X, Y, Z) relative to the coordinate system 32. The pixel 30 would also have two sets of two-dimensional coordinates $(X_1, Y_1)$ and $(X_2, Y_2)$ relative to camera 10 and camera 20 respectively.

In one embodiment, the following algorithm/formula set is used to calculate each pixel's $(X_1, Y_1)$ and $(X_2, Y_2)$ into (X, Y, Z):

$$X = A_1 * X_1 - B_1 * Y_1 + X_{01}$$

$$Y = B_1 * X_1 + A_1 * Y_1 + Y_{01}$$

$(X_1, Y_1)$ is the two-dimensional coordinates relative to Camera 10.

$$X = A_2 * X_2 - B_2 * Y_2 + X_{02}$$

$$Z = B_2 * X_2 + A_2 * Y_2 + Y_{02}$$

$(X_2, Y_2)$ is the two-dimensional coordinates relative to Camera 20.

$A_1, B_1, X_{01}, Y_{01}, A_2, B_2, X_{02}$, and $Y_{02}$ are parameters that need to be determined through calibration. In one embodiment, four pixels in space 33 with known coordinate numbers (X, Y, Z, $X_1, Y_1, X_2$, and $Y_2$) are provided. Applying these known numbers to the formula set above, $A_1, B_1, X_{01}, Y_{01}, A_2, B_2, X_{02}$, and $Y_{02}$ can be determined. Once these parameters are determined, the three-dimensional coordinates (X, Y, Z) of each pixel in the space 33 can be determined based on $(X_1, Y_1)$ and $(X_2, Y_2)$. Accordingly, a database containing the three-dimensional coordinates of every spatial position in a defined space may be established.

In one embodiment, when the tip of a dental instrument 31 enters the space 33, cameras 10 and 20 sense/capture the spatial position of the tip, i.e., determining $(X_1, Y_1)$ and $(X_2, Y_2)$ of the tip, through calculating based on the formula set or referencing the established database, the tip's three-dimensional coordinates may be determined in real time and used to display the tip's position for viewing. If the tip moves, a new set of $(X_1, Y_1)$ and $(X_2, Y_2)$ can be determined, and the system and method described above can calculate and update the tip's position in real time.

Figure 4:
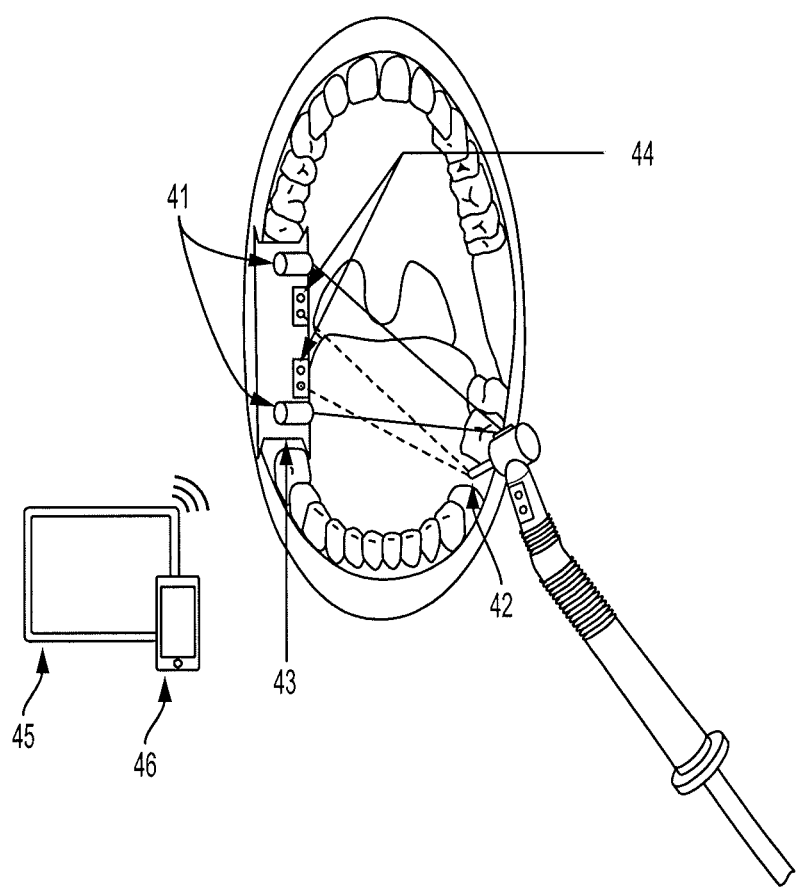
FIG. 4 is a graphic representation of a two-camera intra-oral image sensor-based positioning and navigation device positioned in the patient's mouth.
Figure 5:
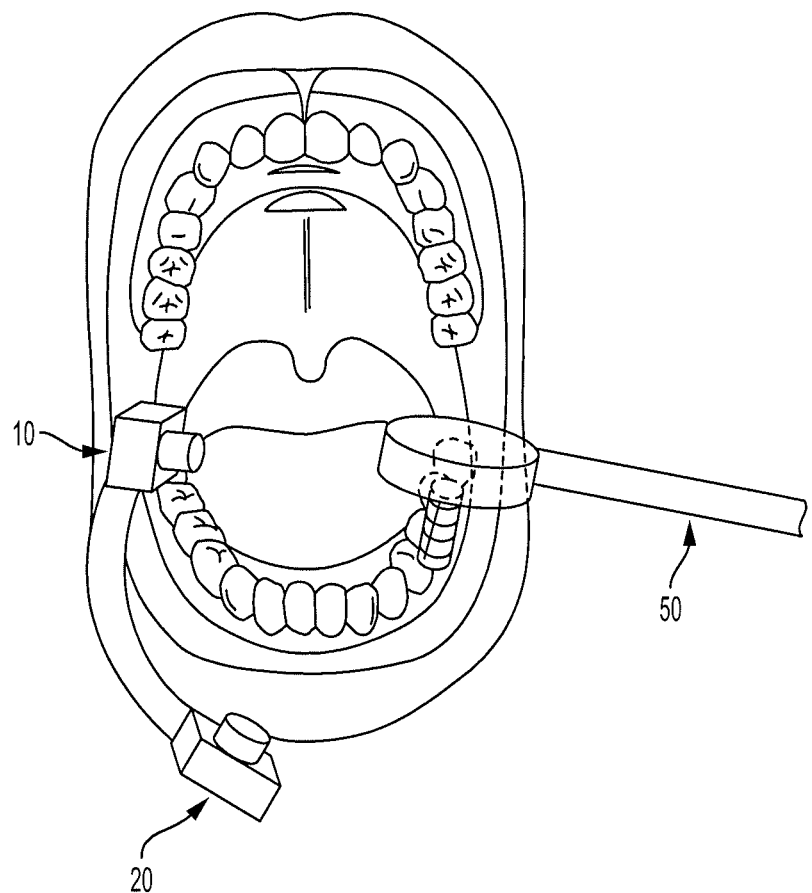
FIG. 5 is another graphic representation of a two-camera intra-oral image sensor-based positioning and navigation device positioned in the patient's mouth

FIG. 4 describes one embodiment of an intra-oral image sensor-based positioning and navigation device having two cameras 41. In one embodiment, the intra-oral image sensor-based positioning and navigation device may also serve as a bite block 43, which may be adjustable and/or customizable, and is positioned in the patient's mouth in order to hold and secure the patient's mouth in position during a dental procedure. The two cameras 41 may sense the tip of a dental instrument 42 and transmit two sets of two-dimensional coordinates, $(X_1, Y_1)$ and $(X_2, Y_2)$, from the cameras 41 to a processor 45 for processing into three-dimensional coordinates (X, Y, Z) and viewing the spatial position of tip 42. The spatial position of tip 42 may also be displayed on a mobile device 46 for viewing. Optionally, the intra-oral image sensor-based positioning and navigation device may also include endoscopes 44 for viewing and/or sensing the patient's oral anatomy. FIG. 5 depicts another embodiment of an intra-oral two-camera positioning and navigation device where cameras 10 and 20 sense the tip of a dental instrument 50 in order to determine the spatial position of the dental instrument 50.

In one embodiment, the intra-oral image sensor-based positioning and navigation device may transmit data relating to the movement and position of dental instruments to an MR lens in order to display on the MR lens for viewing.

The previous description is provided to enable any person of ordinary skill in the art to make or use the disclosed methods and apparatus. Various modifications to these examples will be readily apparent to those skilled in the art, and the principles defined herein may be applied to other examples without departing from the spirit or scope of the disclosed method and apparatus.

The described embodiments are to be considered in all respects only as illustrative and not restrictive and the scope of the invention is, therefore, indicated by the appended claims rather than by the foregoing description. All changes, which come within the meaning and range of equivalency of the claims, are to be embraced within their scope. Skilled artisans may implement the described functionality in varying ways for each particular application, but such implementation decisions should not be interpreted as causing a departure from the scope of the disclosed apparatus and methods. The steps of the method or algorithm may also be performed in an alternate order from those provided in the examples.

The invention claimed is:

1. An intra-oral image sensor-based positioning device for determining spatial coordinates of a dental instrument comprising:

an algorithm for calculating and processing coordinate data, a processor for implementing the algorithm, a storage for storing coordinate data, a first camera, and a second camera wherein the first camera and the second camera are attached to a bite block, wherein:

the first camera having a first field of view: configured to sense and locate a point on a dental instrument on a first plane corresponding to the first field of view; the point on the dental instrument is assigned a first set of two-dimensional coordinates with respect to the first plane;

the second camera having a second field of view; a second plane corresponding to the second field of view wherein the point on the dental instrument is also located on the second plane and is assigned a second set of two-dimensional coordinates with respect to the second plane;

the algorithm configured to provide a three-dimensional coordinates assigned to the point on the dental instrument according to calculation based on the first set of two-dimensional coordinates and the second set of two-dimensional coordinates;

the first set of two-dimensional coordinate points, the second set of two-dimensional coordinate points, and the three-dimensional coordinate points are transmitted to the processor or the storage.

2. A method for determining spatial coordinates of a dental instrument comprising:

providing an algorithm for calculating and processing coordinate data, a processor for implementing the algorithm, a storage for storing coordinate data, a first camera, and a second camera, attaching the first camera and the second camera to a bite block wherein:

the first camera having a first field of view; configured to sense and locate a point on a dental instrument on a first plane corresponding to the first field of view; the point on the dental instrument is assigned a first set of two-dimensional coordinates with respect to the first plane;

the second camera having a second field of view; a second plane corresponding to the second field of view wherein the point on the dental instrument is also located on the second plane and is assigned a second set of two-dimensional coordinates with respect to the second plane;

the algorithm configured to provide a three-dimensional coordinates assigned to the point on the dental instrument according to calculation based on the first set of two-dimensional coordinates and the second set of two-dimensional coordinates;

the first set of two-dimensional coordinate points, the second set of two-dimensional coordinate points, and the three-dimensional coordinate points are transmitted to the processor or the storage.

3. The method for determining spatial coordinates of a dental instrument according to claim 2 wherein the dental instrument communicates with the intra-oral image sensor based positioning device.

* * * * *